United States Patent
Zenz et al.

(10) Patent No.: US 6,960,225 B1
(45) Date of Patent: *Nov. 1, 2005

(54) MEDICAL APPLICATIONS USING MICROCOMBUSTION

(75) Inventors: Carl N. Zenz, Muskego, WI (US); Anil R. Oroskar, Oakbrook, IL (US); Rusty M. Pittman, Chicago, IL (US); Gavin P. Towler, Barrington, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 41 days.

This patent is subject to a terminal disclaimer.

(21) Appl. No.: 10/628,187

(22) Filed: Jul. 28, 2003

Related U.S. Application Data

(63) Continuation-in-part of application No. 10/253,866, filed on Sep. 24, 2002, now Pat. No. 6,832,995, which is a continuation-in-part of application No. 10/200,794, filed on Jul. 22, 2002, now Pat. No. 6,824,555.

(51) Int. Cl.$^7$ .............................................. A61F 7/00
(52) U.S. Cl. ...................... 607/96; 128/898; 606/27; 606/113
(58) Field of Search ..................... 128/898; 606/27–31

(56) References Cited

U.S. PATENT DOCUMENTS

| | | | |
|---|---|---|---|
| 4,290,435 A | 9/1981 | Waggott | 128/800 |
| 4,627,435 A | 12/1986 | Hoskin | 128/303.1 |
| 4,679,561 A | 7/1987 | Doss | 128/422 |
| 4,737,628 A | 4/1988 | Lovoi | 250/226 |
| 4,796,622 A * | 1/1989 | Lu et al. | 606/28 |
| 4,872,458 A | 10/1989 | Kanehira et al. | 128/401 |
| 5,186,181 A | 2/1993 | Franconi et al. | 128/804 |
| 5,251,645 A | 10/1993 | Fenn | 607/154 |
| 5,324,299 A | 6/1994 | Davison et al. | 606/167 |
| 5,354,258 A | 10/1994 | Dory | 601/3 |
| 5,366,456 A | 11/1994 | Rink et al. | 606/16 |
| 5,528,561 A | 6/1996 | Castanis | 368/93 |
| 5,571,098 A | 11/1996 | Domankevitz et al. | 606/15 |
| 5,707,401 A | 1/1998 | Talmore | 607/88 |
| 5,776,175 A | 7/1998 | Eckhouse et al. | 607/100 |
| 6,051,005 A | 4/2000 | Brandsey et al. | 606/148 |
| 6,132,428 A | 10/2000 | VanDusseldorp | 606/46 |
| 6,159,200 A | 12/2000 | Verdura et al. | 606/1 |
| 6,165,184 A | 12/2000 | Verdura et al. | 606/148 |
| 6,235,037 B1 | 5/2001 | East et al. | 606/119 |
| 6,275,738 B1 | 8/2001 | Kasevich et al. | 607/101 |
| 6,312,435 B1 | 11/2001 | Wallace et al. | 606/130 |
| 6,337,998 B1 | 1/2002 | Behl et al. | 607/101 |
| 6,379,347 B1 | 4/2002 | Maki et al. | 606/17 |
| 6,383,179 B1 | 5/2002 | Neuberger | 606/16 |
| 6,394,998 B1 | 5/2002 | Wallace et al. | 606/1 |
| 6,416,524 B1 | 7/2002 | Critz et al. | 606/167 |
| 6,419,684 B1 | 7/2002 | Heisler et al. | 606/170 |
| 2003/0036753 A1 * | 2/2003 | Morgan et al. | 606/32 |

* cited by examiner

Primary Examiner—Roy D Gibson
Assistant Examiner—Henry M Johnson, III
(74) Attorney, Agent, or Firm—John G. Tolomei; Frank S. Molinaro; Arthur E. Gooding

(57) ABSTRACT

A process for delivering high intensity heat in medical applications is disclosed. The process involves forming a mixture of hydrogen and oxygen and reacting the mixture to generate heat near a region of interest.

18 Claims, 1 Drawing Sheet

MEDICAL APPLICATIONS USING MICROCOMBUSTION

CROSS-REFERENCE TO RELATED APPLICATION

This application is a continuation-in-part of application Ser. Nos. 10/253,866 filed Sep. 24, 2002, now U.S. Pat. No. 6,832,995 and Ser. No. 10/200,794, filed Jul. 22, 2002, now U.S. Pat. No. 6,824,555, the contents of which are hereby incorporated by reference.

FIELD OF THE INVENTION

The present invention relates to surgical procedures for delivering intense heat to tissue, and more particularly, the delivery of intense heat through the combustion of hydrogen and oxygen.

BACKGROUND OF THE INVENTION

An essential part of surgery is the ability to make precision incisions. With the incisions, there is the production of blood from cut blood vessels. Procedures for stemming the flow of blood generally involve procedures for cauterizing the bleeding vessels. Among available procedures include the use of lasers, ligation and radio frequency cauterization. Intense heat can also be used for surgical procedures other than cauterization of blood vessels. Localized heat release, or generation, has been achieved by several means. Current approaches for heating tissue include: gamma radiation, lasers, ultrasound, microwave, radio frequency waves, electrical resistance heating, and hot water heating.

A significant drawback to each of these methods is subjecting the body to strong electromagnetic fields and often the surrounding tissue is subjected to the radiation, but in lower doses, or the requirement of a substantial access for inserting the instruments.

Micro-combustion can be used to provide direct heat transfer for local hyperthermia. The use of direct heat transfer overcomes limitations of other methods of hyperthermic treatments by providing a higher heat flux, enhanced localized heat release by fluid exchange, and reduced thermal damage to tissue surrounding a target region. In addition, using micro-combustion requires only a minute opening through which to feed a needle.

SUMMARY OF THE INVENTION

The present invention provides a procedure for using combustion to generate intense heat and apply that heat to tissue for medical treatment. The process comprises forming a mixture; flowing the mixture through a conduit having a delivery end; reacting the mixture proximate to the delivery end to generate heat; and applying the heat to tissue.

Preferably, the mixture comprises stoichiometric amounts of hydrogen and oxygen for the formation of water upon reaction. The mixture composition and amount can be precisely controlled through the use of an electrolyzer for generating the mixture, and through control of electrical power delivered to the electrolyzer to regulate the flow rate.

Other objects, advantages and applications of the present invention will become apparent to those skilled in the art from the following detailed description.

BRIEF DESCRIPTION OF THE DRAWINGS

FIG. 1 is a photograph of a hole generated in a bone using microcombustion.

DETAILED DESCRIPTION OF THE INVENTION

The use of heat, especially high intensity localized heat, is important for several medical applications. The production and application of heat for medical purposes can be supplied through microcombustion. That is, the control of heat release through chemical reactions in a small localized region. The choice of chemicals covers chemicals that are exothermic when reacted. A preferred mixture is one comprising hydrogen and oxygen. The use of microcombustion provides direct heat transfer and overcomes limitations of other methods of hyperthermic treatments by providing a higher heat flux, enhanced localized heat release by fluid exchange, and reduced thermal damage to tissue surrounding a target region. This procedure provides for an inexpensive, convenient and safe control over the delivery of heat to a target tissue.

The use of heat can be applied to any tissue where treatment with heat is appropriate. The use of the term tissue is intended to cover any animal tissue, both soft tissue such as skin, tumors, brain tissue, and hard, or dense, tissue such as bone, and deposits such as kidney stones, etc. The use of heat can be appropriate for other biological entities such as cell tissue cultures, graft organs, skin cells for burn patients, clone cell lines, i.e. HeLa cells, cancer cells, and transplants. The procedures, in addition to medical procedures, are also applicable to veterinary procedures involving mammals, such as cats, dogs, cows, horses, etc., and even non-mammalian animals such as birds, reptiles, amphibians, and fish.

In a preferred embodiment, the procedure includes forming a mixture of hydrogen and oxygen; flowing the mixture through a conduit, wherein the conduit has a supply end and a delivery end; reacting the mixture to generate heat proximate to the delivery end of the conduit; and applying the heat to tissue. Hydrogen and oxygen in the stoichiometric molar ratio of 2:1 provides a gas mixture that combusts without leaving residual gas or undesirable waste products. The mixture is preferably either substantially at stoichiometric, or somewhat oxygen rich. In cases where the heat release is for internal tissue, the preferred ratio is stoichiometric. For heat release applications to external tissue a hydrogen to oxygen molar ratio of less than 2:1 is preferred, or an oygen rich mixture. The only product as a result of the combustion is water which can be absorbed by the tissue, or drained from the area of application. Usually the amount of water generated will be of a small enough quantity that the body can readily absorb it. For the situation where the mixture is oxygen rich, the oxygen will be absorbed by the tissue.

The delivery end of the conduit is placed proximate to the target tissue that is to be treated. The heat generated then heats the target tissue. The heat is controlled to heat the target tissue to a desired range while limiting the temperature rise of the surrounding tissue. One method of delivery of heat to the target tissue requires injecting the delivery end of the conduit, or needle, through any surrounding tissue and into the target tissue. An example target tissue is a tumor mass. The cells in the tumor mass can be killed by heating the cells to a temperature in the range of about 43° C. to about 47° C., while keeping the surrounding tissue below 43° C.

Heat can be used to fragment kidney stones to allow passage of the fragments, and heat can be used to breakup, or fragment, gallstones, also known as biliary calculi, to allow removal of the gallstone fragments with a system to flush the fragments from the gall bladder. The heating of gallstones with intense heat can fragment gallstones.

Removal of tissue is performed by ablation of tissue on the surface of the patient, that is, by applying precisely controlled heat release to tissue. This is a burning away of the tissue that is external tissue, for example warts or tattoo removal. Application of intense heat can be used in the removal of tonsils or adenoids. Internal tissue can be removed also, such as using a catheter with a needle attached to position the needle's tip near plaque on an arterial wall. Removal of the plaque by heating is an alternative to implanting a stent or scraping of the arterial walls.

In addition to the above mentioned tissues, heat can be applied to cataracts; plaque; dental tissue; tonsils; adenoids; bone tissue; sarcomas; cartilaginous tissue, i.e. meniscii; connective tissue such as tendons and ligaments; muscles; neurons; keratin cells, i.e. finger and toenails; adipose tissue; cardiac tissue including heart valves; intestinal tissue, i.e. polyps; pulmonary tissue; lymphoid tissue; and reproductive tissue, i.e. gonads.

Instruments for applying intense heat to tissue are described in U.S. patent application Ser. No. 10/200,794, filed Jul. 22, 2002, which is incorporated by reference in its entirety.

The use of heat can also be used as an alternate method of cutting tissue. Intense heat can be used to burn, or ablate tissue, to create a small hole in material such as bone tissue. The creation of a small hole in a bone can provide access to the underlying tissue. The use of heat eliminates the formation of bone fragments, and cauterizes blood vessels at the same time the cutting is performed. This procedure also permits cutting where mechanical cutting is difficult due to location or because of the bones being readily subject to collateral damage. The procedure applies no pressure, and subsequently no shear stresses are created in the bone during the procedure, as well as a minimum of damage to surrounding tissues. Tests showing the procedure of cutting bone, i.e. using a bone from a cow, demonstrates the ability to use this procedure/technique. As shown in FIG. 1, a hole 10 has been drilled into a bone 20 of a couple of millimeters in diameter with only slight damage 30 to the surrounding bone tissue. The bone is positioned next to a scale in centimeters. The hole 10 has a generally circular shape with a diameter of approximately 0.5 cm, and is white due to residual ash in the hole 10. The hole 10 does not go all the way through the bone 20. There is a slight amount of charring 30 of the surrounding area of the bone. The procedure involves forming a mixture of hydrogen and oxygen; delivering the mixture through a capillary with an internal diameter of about 200 micrometers, reacting the mixture at the tip of the capillary and applying the combusting mixture to the bone. The heat causes a breakdown of the bone and the capillary is advanced through the bone, forming a hole. There are no splinters produced and the reaction products are biologically harmless.

Many surgical procedures produce bleeding when tissue is cut, making an incision for access to organs underneath the tissue, or during a resection due to cutting of small blood vessels. The bleeding presents problems such as interfering with the surgical field of vision, as well as creating a nidus for infectious agents. Additionally, severe hemorrhagic and hypovolemic shock may occur from trauma and concurrent surgery such as splenic or other organ ruptures. The concomitant cauterizing of these blood vessels reduces bleeding (provides hemostasis) and facilitates the surgeon's task. Providing controlled intense heat at the incision enables the cauterization during the cutting. A mixture of hydrogen and oxygen is formed; the mixture flows through a conduit to a delivery end of the conduit; the delivery end is positioned near the cutting edge of the cutting instrument; and the mixture flows over a catalyst positioned near the delivery end of the conduit and reacts to generate heat. The heat generated is controlled by the flow rate of the mixture through the conduit. The design of instruments using this procedure are described in U.S. patent application Ser. No. 10/253,866, filed Sep. 24, 2002, which is incorporated by reference in its entirety.

Fractured bones can be bonded with epoxy resins or glues. The use of thermoset glue or resin requires the addition of heat to cure the thermoset glue or resin. Using a localized intense heat source allows the application of thermosets. The process for using a localized heat source includes injecting a liquid thermoset material to a target, such as the surface of a fractured bone. A conduit having a supply end and a delivery end is inserted such that the delivery end of the conduit is positioned next to the injected liquid thermoset material. A mixture of hydrogen and oxygen is delivered to the supply end of the conduit, and flows along the conduit to the delivery end. A catalyst is disposed proximate to the delivery end of the conduit, and as the mixture flows over the catalyst, the hydrogen and oxygen react generating heat to cure the thermoset.

For producing a stronger thermoset, the thermoset can include reinforcing fibers, such as carbon fibers, to add strength to the cured thermoset.

The mixture can be formed in numerous ways. One method of forming the mixture is to electrolyze water and allow the gases to mix directly in the electrolyzer. An electrolyzer provides the exact stoichiometric ratio of hydrogen to oxygen in the decomposition of water. This provides for an inexpensive electrolyzer, as the electrolyzer can be designed to not separate the gases thereby reducing cost of manufacture. An optional method of obtaining the mixture is metering hydrogen gas and oxygen gas from gas cylinders.

The mixture can be formed by mixing hydrogen and oxygen gas in a micromixer. The micromixer must be sized such that the mixture will be outside the combustion limits when in the micromixer. A micromixer will preferably be designed to minimize pressure losses, and a micromixer of a design using multilamination mixing can be found in U.S. application Ser. No. 09/850,439, filed on May 7, 2001, and is incorporated by reference in its entirety.

The mixture is delivered from a supply through a conduit to the delivery end of the conduit where the mixture reacts to generate heat. The conduit is sized to contain the mixture and keep the mixture outside the combustion limits. Since the procedure is to deliver heat to tissue that often will be surrounded by external tissue, the conduit preferably includes a portion that is a hollow tube having sufficient rigidity to allow penetration of the external tissue. The conduit needs to have good thermal stability, particularly in proximity to the delivery end. The conduit can be made of any material that will not melt or soften when in use, and can be exposed to temperatures at the delivery end of up to about 120° C. An example of a conduit is a steel needle. The conduit can be made of thin walled metals such as stainless steel, aluminum, copper, etc., ceramic coated polymers, ceramic polymer compositions, polypropylene, PEEK, Teflon™, nylon, etc. or combinations thereof. An example of a conduit including a combination of materials is a conduit having a length of a flexible thermoplastic, that can withstand moderate temperatures, affixed to a steel needle, wherein the steel needle is of sufficient length to prevent the temperature of the thermoplastic rising to where the thermoplastic melts or softens.

For the preferred mixture of hydrogen and oxygen, the conduit will have an effective diameter of less than 400 micrometers (0.4 mm), and more preferably an effective diameter of about 200 micrometers. One option for a needle having a larger inner diameter is for the needle to be filled with a porous media, wherein the porous media has channels having effective diameters of less than 400 micrometers, and wherein a portion of the porous media proximate to the delivery end of the needle has a catalyst deposited thereon.

The mixture of hydrogen and oxygen can be provided from independent supplies of hydrogen and oxygen, wherein each supply is metered and controlled to produce a mixture having a desired molar ratio of hydrogen to oxygen in the range from about 2:1 to about 1:1, with a preferred molar ratio of hydrogen to oxygen at about 2:1. One method of obtaining molar ratios of less than 2:1 is by addition of oxygen to a mixture generated by an electrolyzer. Another method includes collecting the gases separately and remixing to a desired ratio. For ratios of less than stoichiometric, additional oxygen can be used to oxygenate tissue proximate to the tissue being heated.

The mixture flows over a catalyst to react the hydrogen and oxygen and generate heat. The use of a catalyst to facilitate the reaction allows for initiating the reaction after the delivery end of the conduit has been position proximate to the target tissue. Catalysts that facilitate the reaction include, but are not limited to, catalysts comprising a metallic catalytic material wherein the metallic catalytic material is at least one metal selected from scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), and mercury (Hg).

Optionally, the mixture flows to the delivery end of the conduit where a reaction of hydrogen and oxygen is initiated. The reaction can be initiated by heat, a flame or a spark supplied by an external source, and wherein the reaction is self sustaining and continues after initiation.

Advantages of this procedure include easy and precise control of the generation of intense heat; the hydrogen flame can be narrowly focused for precise control of heating; and the process does not generate electromagnetic fields that can be detrimental to patients with pacemakers.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the controlled delivery of intense heat in medical, veterinary procedures, or biological research laboratories comprising the steps of:

forming a mixture containing hydrogen and oxygen;
   flowing the mixture through a conduit having a supply end and a delivery end;
   reacting the mixture in the presence of a catalyst proximate to the delivery end to generate heat; and
   applying the heat to tissue.

2. The process of claim 1 wherein the tissue comprises tissue selected from the group consisting of tumors, warts, cataracts, plaque, kidney stones, gallstones, dental tissue, tonsils, adenoids, bone tissue, sarcomas, cartilaginous tissue, connective tissues, muscles, neurons, keratin cells, adipose tissue, cardiac tissue, intestinal tissue, pulmonary tissue, lymphoid tissue, and reproductive tissue.

3. The process of claim 1 wherein the heat removes a predetermined number of tissue layers.

4. The process of claim 1 wherein the heat cauterizes blood vessels.

5. The process of claim 4 further comprising the step of cutting the tissue.

6. The process of claim 5 wherein the tissue is cut using the heat.

7. The process of claim 5 wherein the tissue is cut using a cutting blade and then cauterized using the heat.

8. The process of claim 1 wherein the heat is used to cauterize neurological synaptic regions.

9. The process of claim 1 wherein the conduit has an effective diameter of less than 400 micrometers.

10. The process of claim 9 wherein the conduit has an effective diameter of about 200 micrometers.

11. The process of claim 1 further comprising the step of dissociating water to form hydrogen and oxygen, before the mixing step.

12. The process of claim 1 wherein the catalyst comprises at least one catalytic metal selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), and mixtures thereof.

13. The process of claim 1 wherein the step of reacting the mixture includes initiating the reaction.

14. The process of claim 13 wherein the initiation occurs by supplying heat or a spark.

15. The process of claim 1 further comprising the step of flowing hydrogen and oxygen prior to the step of forming a mixture, wherein the flow rates of the hydrogen and oxygen are controlled.

16. The process of claim 1 further comprising the step of controlling the ratio of hydrogen to oxygen in the mixture.

17. The process of claim 1 further comprising the step of controlling the flow rate of the mixture.

18. The process of claim 17 wherein the flow rate is controlled by electrical power.

* * * * *